United States Patent [19]

Perbellini et al.

[11] Patent Number: 5,503,848
[45] Date of Patent: Apr. 2, 1996

[54] SPONGY MATERIAL CONSISTING ESSENTIALLY OF HYALURONIC ACID OR ITS DERIVATIVES, AND ITS USE IN MICROSURGERY

[75] Inventors: Alberto Perbellini, Padua; Gino Toffano, Montegrotto Terme; Aurelio Romeo, Rome, all of Italy

[73] Assignee: Fidia S.p.A., Abano Terme, Italy

[21] Appl. No.: 925,073

[22] Filed: Aug. 5, 1992

[30] Foreign Application Priority Data

Aug. 5, 1991 [IT] Italy .................................. MI91A2207

[51] Int. Cl.⁶ .......................... A61K 31/725; A61K 9/00
[52] U.S. Cl. .................... 424/488; 424/78.05; 424/78.06; 424/78.37; 424/DIG. 7; 424/437; 424/400
[58] Field of Search ..................................... 424/484, 488, 424/78.06, 78.05, 78.37, DIG. 7, 437

[56] References Cited

U.S. PATENT DOCUMENTS

| | | | |
|---|---|---|---|
| 4,411,988 | 10/1983 | Toth et al. | 435/7 |
| 4,490,351 | 12/1984 | Clark, Jr. | 424/5 |
| 4,703,108 | 10/1987 | Silver et al. | 424/485 |
| 4,851,521 | 7/1989 | della Valle et al. | 536/55.1 |
| 4,965,353 | 10/1990 | della Valle et al. | 536/55.1 |

FOREIGN PATENT DOCUMENTS

| | | |
|---|---|---|
| 0138572 | 10/1984 | European Pat. Off. . |
| 0193510 | 2/1986 | European Pat. Off. . |
| 0216453 | 7/1986 | European Pat. Off. . |
| 2650180 | 7/1990 | France . |
| 2235204 | 2/1991 | United Kingdom . |
| 8905645 | 6/1989 | WIPO . |

OTHER PUBLICATIONS

"ACTA Oto–Laryngologica" vol. 110, No. 1–2, 1 Aug. 1990, Stockholm pp. 110–114.
"American Journal of Otolaryngology" vol. 7, No. 3, Jun. 1, 1986 pp. 181–186.
J. Theor. Biol. (1986) 119, 219–234: P. Weigel et al.: A Model for the Role of Hyaluronic Acid and Fibrin in the Early Events during . . . .
Lars–Eric Stenfors et al.: Exogenous Hyaluronic Acid (Healon) Accelerates the Healing of Experimental Myringotomies.
Am. Journ. of Otolaryngology pp. 181–186 7:1986: C. Laurent et al.: Hyaluronic Acid Reduces Connective Tissue Formation in Middle Ears Filled . . . .
Joint International Meeting: 3rd Meeting on Side Effects of Anti–Inflammatory Analgesic Drugs and 13th European Workshop on Inflammation: Verona (Italy) May 1991.
A. Martini et al.: Allegato N. 4: Hyaluronic Acid as Treatment of Tympanic Membrane Perforation . . . .
Acta Otorhinol, Ital., 10, 559–577, 1990: A. Martini et al.: Experimental Tympanic Membrane Perforation: natural history of healing process in rat.

*Primary Examiner*—Edward J. Webman
*Attorney, Agent, or Firm*—Birch, Stewart, Kolasch & Birch

[57] ABSTRACT

The present invention relates to a new spongy material consisting essentially of hyaluronic acid or its derivatives. The characteristics of the new pharmaceutical preparations consist in assuring high concentrations of active principle for a long period of time, by exploiting the characteristics of slow release of the active principle.

The new pharmaceutical preparations can be utilized advantageously in all the numerous situations of microsurgical practice (in particular the ones relating to ear or in odontostomatology), in which it is necessary to use a substance that can be metabolized by the organism and is capable of making easier flap take, reepithelialization of mucous membranes, stabilization of grafts and filling of cavities.

The specific use of the new pharmaceutical preparations is particularly important and useful in the various ear pathologies and in the practice of otologic, otoneurosurgical and odontostomatological microsurgery, such as for instance repair of tympanic perforations.

13 Claims, 1 Drawing Sheet

SPONGY MATERIAL CONSISTING ESSENTIALLY OF HYALURONIC ACID OR ITS DERIVATIVES, AND ITS USE IN MICROSURGERY

FIELD OF THE INVENTION

The present invention relates to a new spongy material consisting essentially of hyaluronic acid or its derivatives. For better evidence and simplicity the abbreviation lyophilized HA will be used in the following text to indicate the spongy material consisting of hyaluronic acid or its derivatives, whereas the abbreviation IAL solution will be used to indicate the 1% solution of hyaluronic acid sodium salt.

DESCRIPTION OF RELATED ART

Hyaluronic acid

Hyaluronic acid is a natural heteropolysaccharide consisting of alternate residues of D-glucuronic acid and N-acetyl-D-glucosamine. It is a linear polymer having a molecular weight ranging between 50.000 and 13 millions, depending on the source it is obtained from, on the method of preparation and methods of determination; in the natural state it is present in the pericellular gels, in the basic substance of the connective tissues of the vertebrate organisms (of which it is one of the main components), in articular synovial liquid, in vitreous humour, in the tissue of human umbelical cord and in cock's combs.

Specific fractions of hyaluronic acid are known, having a definite molecular weight and which do not present any inflammatory activity and therefore can be used to make the cicatrization easier or to replace the endobulbar liquids or for the therapy of pathologies in the joints by means of interarticular injections, as disclosed in European patent n. 0138572 granted to the Applicant on Jul. 25, 1990.

Esters of hyaluronic acid, in which all the carboxylic groups of the acid or part of them are esteriliad, as well as the use of said esters in the pharmaceutical, cosmetic field and in the field of the biodegradable plastic materials, are also known, as disclosed in U.S. Pat Nos. 4,851,521 and 4,965,535 granted to the Applicant respectively on Jul. 25, 1989 and on Oct. 23, 1990.

It is known that hyaluronic acid plays an essential part in the processes of tissue repairs, mostly in the early steps of the process of granulation tissue formation, by stabilizing the clot matrix and by controlling its degradation, by promoting the call of inflammatory cells such as polymorphonucleates and monocytes, of mesenchymal cells, such as fibroblasts and endothelial cells and by orienting the subsequent migration of the ephitelial cells.

It is known that the administration of solutions of hyaluronic acid can accelerate the recovery of patients having bed-sores, wounds and scalds.

The role of hyaluronic acid in the several steps forming the process of tissue repair was disclosed, by construction of a theoretical model, by Weigel P. H. et al.: A model for the role of hyaluronic acid and fibrin in the early events during the inflammatory response and wound healing" J. Theor. Biol., 119:219,1986.

Hyaluronic acid and its otologic application

Experimental research works are known on rats subjected to myringotomies (Stenfors L. E. et al.: Exogenous hyaluronic acid accelerates the healing of experimental myringotomies, Auris Nasus Larinx, 12 (suppl.1): 214,1985), which showed that the local application of solutions of hyaluronic acid at the border level of the tympanic perforation, produces a quicker and more complete healing of the lesion, showing the effectiveness of hyaluronic acid in repairing tympanic lesions.

Other studies showed that the application in middle ear of solutions of hyaluronic acid mixed with an absorbable gelatin sponge, reduces the formation of cicatricial adhesions, contrary to what was noted, only when absorbable gelatin sponges were used (Laurent C. et al.: Hyaluronic acid reduces connective tissue formation in middle ears filled with absorbable gelatin sponge: an experimental study. Am. J. Otolaryingol., 7: 181, 1986).

In these last years many experimental and clinical studies were carried out, in order to evaluate the effectiveness and tolerance of sodium hyaluronate solution (registered as pharmaceutical speciality in the assignee's name) in the treatment of tympanic perforations. In particular in a recent study on an experimemntal model concerning lesion of rat tympanic membrane, assignee's researchers, in co-operation with other researchers, carried out a morphological evaluation or tympanic membrane repair after application or IAL solution, in comparison with a spontaneous repair.

The results obtained in this study show that, tympanic membrane repair occurs on account or a true granulation tissue and that the administration of IAL solution produces in the animals an increase in the percentage of repaired tympanic membranes and a more regular development of the physiological repair steps (Govoni et al.: "An experimental approach to the biology of the healing process of tympanic membrane perforation: comparative morphological evaluation of spontaneous versus hyaluronic acid-modulated repair" 3rd Meeting on side effects of anti-inflammatory analgesic drugs and 13th European Workshop on inflammation. Verona, May 8–11, 1991).

In an experimental study on rats, a morphological and electrophysiological evaluation was carried out, in order to evaluate the potential ototoxicity of an IAL solution in comparison with methylcellulose, after direct administration of both compounds into rat middle ear. In accordance with the literature, the transitory auditire loss of transmissive type, which occurs after injection of IAL solution or methycellulose in rat middle ear was confirmed. The morphological analysis of middle ear shows a transitory call of inflammatory cells in both treatment groups and a diffuse degeneration of the epithelial cells only in the group treated with methylcellulose (Martini A. et al.: Hyaluronic acid as treatment of tympanic membrane perforation. A study of potential ototoxicity of hyaluronic acid in comparison with methylcellulose. Meeting 1st–4th Sep. 1991 in York, Collegium oto-rhino-laryngologicum Amicitiae Sacrum).

Up today only pharmaceutical compositions have been described, containing hyaluronic acid and its esterified derivatives in the form of solutions, creams or capsules for the subcutaneous implantation.

A spongy material, consisting of hyaluronic acid or its derivatives, was never described.

The main problem, which, up today, was not solved, is that in all the numerous situations of microsurgical practice, in which the use is necessary of a substance which can be metabolized by the organism and is capable of making easier flap take, reepithelialization of mucous membranes, stabilization of grafts or filling of cavities (in particular in tympanic repairs), the administration of hyaluronic acid solutions needs an inert carrier, for instance little sponges of methylcellulose or gelatin or a conveyance in the form of cream.

The presence of a carrier such as methylcellulose can contribute to the development of local phlogistic reactions and of cicatricial and/or adhesional outcomes; moreover should methylcellulose be released by the carrier in the soluble form, by penetrating into middle ear, it could, as shown in the above-mentioned study, cause a temporary loss of hearing and a degeneration of the epythelial cells of middle ear.

The direct employment of hyaluronic acid solutions, besides causing the humidification of the area to be treated, and therefore its steeping, does not allow the controlled release of the active principle, which therefore has too short stay-times on the lesion and must be administered repeatedly.

Now we have found that, the new spongy material consisting of hyaluronic acid or its derivatives, according to the present invention, allows to avoid all the above-mentioned drawbacks. The pharmaceutical preparations, according to the present invention, can be used advantageously and represent a remarkable progress in the microsurgery field, in particular the microsurgery of middle ear and tympanic repair, and present many advantages in comparison with the pharmaceutical preparations and materials which have been used up today, besides in comparison with the use of hyaluronic acid solutions.

In fact, the spongy preparations of lyophilized HA, according to the present invention, allow to reduce the number of applications to be carried out and to avoid the self-dressing by the patient, by simplifying the application of said preparation and reducing the risk that the patient could produce, during the application, new traumas in the tympanic membrane or that he does not respect the optimum of the application conditions in asepsis.

Moreover they allow to avoid the humidification of the external auditory duct and of the eardrum, by reducing remarkably the possible phlogistic reactions, in particular of middle ear and of external ear and avoid the steeping, in particular of the skin covering the external auditory duct.

A further advantage of such preparation, according to the present invention, consists in allowing to avoid the use of some substances such as methylcellulose, which are supposed to be biologically inert, but can give rise to the formation of local phlogistic reactions and of cicatricial and/or adhesional outcomes, which are often caused by these substances, such as for instance gelatine sponges.

The pharmaceutical preparations, according to the present invention, consisting essentially of esters of hyaluronic acid, present the further advantage of releasing the active principle slowly and therefore of requiring only one administration, with evident huge advantages for patients, chiefly children, for the physician and for the health services.

For these reasons they are particularly useful in all the situations, in which it is necessary to protract the stay times of the pharmaceutical preparations in the tissues, in order to allow the anatomical structures to consolidate their own organization and their own connections with the adjacent structures.

The spongy material, consisting essentially of hyaluronic acid or its derivatives, which forms the object of the present invention, from a macroscopic point of view, appears as a higly microporous spongy little disk, being preferably between 0.2 and 2 cm high, having a diameter ranging preferably between 0.5 and 4 cm, having a residual humidity content ranging between 0.01% and 10%, being very hydrophilic and easily manageable, which spongy material, after having been compressed, can assume the shape of a discold , which is still sufficiently elastic so that it can be applied easily and brought into contact with the lesion to be treated.

The preparation of the finished product in the form of a spongy material is carried out by a lyophilisation process, starting from dilute solutions of active principle.

In order to show the characteristics of the spongy material, according to the present invention, as well as its pharmaceutical effectiveness, we will report two studies carried out by us in comparison with IAL solution.

A—Clinical effectiveness and local and general tolerance of the topical application of lyophilized HA, in comparison with 1% IAL solution, in subjects having a tympanic perforation.

The study, as described hereinafter, evaluates the effectiveness of lyophilized IAL, in comparison with 1% IAL solution (whose active principles are disclosed in European Patent EP n. 0138572, granted in the name of the Applicant on Jul. 27, 1990), in making the process of tympanic repair easier.

The following parameters have been considered as the main evaluation parameters:

1) number of complete tympanic repairs;
2) repair time.

MATERIALS AND METHODS

Experimental procedure

Figure 1:
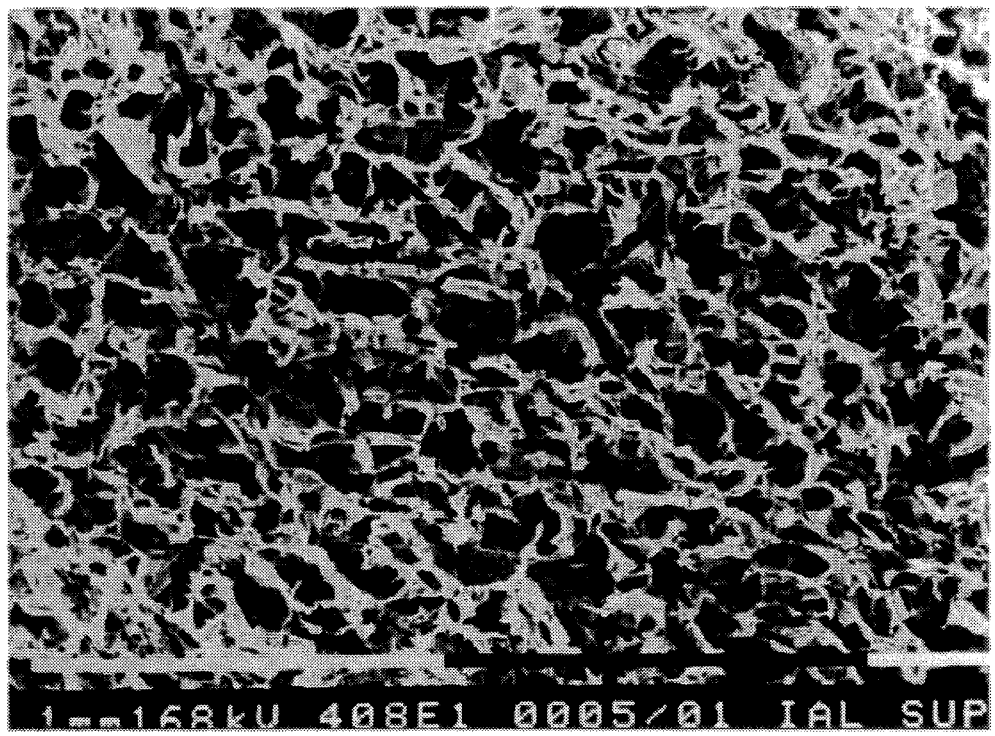
FIG. 1 is a scanning election photograph of a spongy material obtained from HA, wherein the white bar represents 1 mm.

The study is multicentric, open, controlled lyophilized HA vs IAL solution, with random assignment of the patients to one of the two treatment groups.

Within the limits of such study 56 patients were engaged (24 men and 37 females, whose age ranged between 13 and 75 years; 30 of them were random assigned to the treatment group with lyophilized HA and 26 to the treatment group with IAL solution. Patients of both sexes were admitted to the study; they were more than 12 years old and had a monolateral consolidate tympanic perforation of traumatic or inflammatory etiology, present for a period of time equal to two months or over, and having a lesion size which was not above 40% of pars tense. From the study, patients were excluded presenting one or more of the following exclusion criteria: a) paramarginal tympanic lesions having a size above 2 mm2; b) pathologies in progress concerning middle and/or external ear (or serious pathologies in progress which could interfere with the repair process); c) use of cicatrizing drugs different from the drugs which had been foreseen for the study or drugs which could interfere with the process of tissue repair (for instance cortisone); outcomes of previous myringo-tympanoplastic surgical operations.

The patients were assigned, according to the random list, to one of two treatment groups (either to the group treated with lyophilized HA or to the group treated with IAL solution).

Case enumeration

The main characteristics of the patients under examination, subdivided in the two tratment groups, are summarized in Tables 1–7.

TABLE 1

Demographic characteristics

|  | HA lyophilized | IAL solution |
|---|---|---|
| Patients | 30 | 26 |
| sex: |  |  |
| men | 14 | 10 |
| females | 16 | 16 |
| Age (years) |  |  |
| X ± S.D. | 35,0 ± 16,1 | 38,8 ± 18,8 |
| range | 15 to 62 | 13 to 75 |

TABLE 2

Stay time of the tympanic wound

|  | HA lyophilized | IAL solution |
|---|---|---|
| 2 < months ≦ 6 | 6 | 4 |
| 6 < months ≦ 12 | 3 | 3 |
| months > 12 | 20 | 19 |

TABLE 3

Starting size of the wound

|  | HA lyophilized | IAL solution |
|---|---|---|
| mm² (X ± S.D.) | 8.84 ± 8.5 | 9.0 ± 6.3 |

(ϕgreater × ϕ smaller)

TABLE 4

Quadrants, wound location

|  | HA Lyophilized | IAL solution |
|---|---|---|
| Fore-upper | — | 4 |
| Fore-lower | 6 | 4 |
| Hinder-upper | 8 | 2 |
| Hinder-lower | 5 | 5 |
| Multiple locations | 11 | 11 |

TABLE 5

Wound location

|  | HA lyophilized | IAL solution |
|---|---|---|
| Central | 14 | 13 |
| Marginal | 4 | — |
| Paramarginal | 12 | 13 |

TABLE 6

Wound shape

|  | HA lyophilized | IAL solution |
|---|---|---|
| Linear | — | 1 |
| Reniform | 8 | 7 |
| Roundish | 22 | 18 |

TABLE 7

Wound cause

|  | HA lyophilized | IAL solution |
|---|---|---|
| Traumatic | 8 | 8 |
| Phlogistic | 22 | 18 |

Treatment conditions

The patients, after dysepithelization operation of the tympanic wound edge, under local anaesthesia conditions, were subjected to the following procedures:

* Group A: IAL solution

At the end of the operation, the physician started the application to the external auditive duct, and well in contact waith the tympanic membrane, of a methylcellulous little tampon (Merocel®) medicated with IAL solution.

The patient provided for daily self-dressings, for the subsequent six days, by placing 0.5 ml of IAL solution in the external auditive duct by means of an insulin syringe without needle.

The little tampon was removed on the 7th day by the experimenter, who provided for the otoscopic tests of the wound.

In the case or complete healing of the wound, the patient was invited to come back on the 14th day for a further and final clinical examination, during which a tympanogram was carried out as well.

If, on the 7th day, the otoscopic test did not show a complete repair of the tympanic perforation, the experimenter applied a new medicated tampon to the patient external auditive duct, under the same conditions, as described hereinbefore.

Then the patient provided for the self-dressing for the subsequent six days (8th –13th day) coming back to be checked on the 14th day.

* Group B: lyophilized HA

The experimenter, after the operation, provided to apply lyophilized HA in contact with the tympanic membrane, then repeating the dressing on the 4th day. The wound otoscopic test was carried out on the 7th day.

In the case of complete wound healing, the patient was invited to come back on the 14th day for a further and final clinical examination, during which a tympanogram was carried out as well.

If, on the 7th day, the otoscopic test did not show a complete repair of the tympanic perforation, the experimenter provided for a further dressing cycle on the 7th and 10th day.

On the 14th day an otoscopic test was carried out, verifying the therapy results.

For both groups (A and B) the study foresaw four obligatory controls and finished on the 28th day with a last clinical examination, to which the patient was subjected.

Evaluation criteria

Before starting the treatment, a series of surveys concerning private data, anamnesies and routine laboratory tests, was carried out.

In particular one observed: otorhinolaryngology objectivity, presence expressed in days and months of the tympanic wound, etiology of the tympanic wound, otoscopic test specifying the laterality, quadrant, location and shape of the tympanic wound to be treated, wound size expressed in mm, which was calculated by measuring at otomicroscopy the two greatest diameters of the tympanic perforation, tonal audiometric test.

The examinations were carried out on the 7th, 14th, 21st and 28th day from the start of the treatment.

The following surveys were carried out:

1—otoscopic test;
2—survey of the complete wound repair which might have taken place;
3—size of the residual wound, in the case of incomplete repair;
4—tonal audiometric test;
5—tympanogram (in the case of perforation repair);
6—clinic judgement relating to the treatment effectiveness expressed as follows:
   very good: complete wound repair, standard tympanogram;
   good: complete wound repair, altered tympanogram;
   fair: partial reduction and above 50% of the starting size of the wound;
   insufficient: partial reduction and below 50% of the starting size of the wound;
   no: no change in the size of the wound;
   a negative: presence of inflammatory and/or contagious processes.

As to tympanogram, the different types of tympanogram were classified, according to Jerger's classification, as follows:

type A corresponding to a normal type, with bell-shaped curve and peak of maximum compliance at 0 mm $H_2O$;
type $A^1$ with bell-shaped curve, peak of maximum compliance at 0 mm $H_2O$ and reduced compliance;
type B with flat curve, very reduced compliance and absence of peak of maximum compliance;
type C with normal compliance and peak of maximum compliance shifted to pressure negative values;
type D with "W" morphology and "W" interpeak distance below 100 mm $H_2O$;
type E with camel's hump morphology and interpeak distance above 100 mm $H_2O$;

RESULTS

The therapeutic activity of the tested preparations was evaluated, according to the number of complete tympanic repairs and to repair time.

1) Number of complete tympanic repairs

In table 8 the data are set forth concerning the number of tympanic perforations, which, in the two treatment groups, proved to be completely repaired, partly repaired or unchanged.

TABLE 8

| | Otoscopic objectivity | |
| --- | --- | --- |
| | HA lyophilized | IAL solution |
| Treated cases | 30 | 26 |
| Complete repairs (no. and %) | 17 (56.6) | 13 (50.0) |
| Partial repairs (no. and %) | 11 (36.6) | 9 (34.6) |
| Unchanged perforations (no. and %) | 2 (6.6) | 4 (15.3) |

The data show that:

a—in the group treated with lyophilized HA, 17 patients out of 30 tested patients, achieved a complete repair of the tympanic wound, with a success percentage of 56.6%; 11 achieved a partial repair, with a percentage of 36.6% and 2 patients presented an unchanged perforation (6.6%).

b—in the group treated with IAL solution, 13 out of 26 tested patients achieved a complete repair of the tympanic wound (50.0%), 9 achieved a partial repair (36.6%), and 4 patients presented unchanged perforation (15.3%).

2) Time of tympanic repair

In Table 9 the data are set forth, relating to the time of tympanic repair in the group treated with lyophilized HA and in the group treated with IAL solution.

TABLE 9

| | Time of tympanic repair - complete repairs | | | | |
| --- | --- | --- | --- | --- | --- |
| | Total | 7th | 14th | 21st | 28th |
| Lyophilized HA | 17 | 10 (58.8) | 6 (35.3) | 1 (5.9) | — |
| IAL solution | 13 | 3 (23.1) | 8 (61.5) | 2 (15.4) | — |

The percent value is indicated between brackets

The data show that:

a—in the group treated with lyophilized HA, out of 17 patients with complete repair of the tympanic perforation, 10 patients showed that the repair had occurred on the 7th day (I control), 6 patients on the 14th day (II control) and 1 patient on the 21st day (III control);

b—in the group treated with IAL solution, out of 13 patients with complete repair of the tympanic perforation, 3 patients showed that the repair had occurred on the 7th day (I control), 8 patients on the 14th day (II control) and 2 patients on the 21st day (III control) . . . pa Tympanometric evaluations In Table 10 the data are set forth, relating to the type of tympanogram noted in the patients who, in the two treatment groups, have achieved complete repair of the tympanic membrane.

TABLE 10

| | Tympanogram | |
| --- | --- | --- |
| | Lyophilized HA | IAL solution |
| Complete repair | 17 | 13 |
| Normal type A | 11 (64.7) | 10 (76.9) |
| Altered type $A_1$-D | 5 (29.4) | 2 (15.9) |
| Altered type B | — | 1 (7.7) |
| Not carried out | 1 (5.9) | — |

The percent value is indicated between brackets

The data show that:

a—in the group treated with lyophilized HA, 11 patients, out of 16 subjected to tympanometry, presented a tympanogram of type A (normal), according to Jerger; in the other 5 patients a tympanogram of type $A_1$-D was noted;

b—in the group treated with IAL solution, 10 patients, out of 13 patients subjected to tympanometry, presented a tympanogram of type A (normal), according to Jerger, 2 patients presented a tympanogram of type $A_1$-D and in one patient a tympanogram of B type, according to Jerger, was noted.

Tolerance

The general tolerance proved to be very good in both treatment groups; in no patient, in fact, adverse reactions of systemic type were noted; the two treatments proved to be well tolerated locally as well.

B—Effectiveness of a lyophilized pharmaceutical preparation or an estereal derivative or hyaluronic acid in the repair process or rat tympanic membrane.

GOAL

The study, as described hereinafter, evaluates the effectiveness of a lyophilized pharmaceutical preparation of an estereal derivative of hyaluronic acid and precisely of the ethyl ester of hyaluronic acid (identified by abbreviation HYAFF7 and disclosed in European patent application EPA 216 453 filed on Apr. 1, 1987), in making easier the repair process or tympanic membrane in the experimental model or diabetic rat.

The diabetic rat was selected, as it represented a better experimental model, compared with a sound rat: in fact, in a diabetic rat the healing times are sufficiently longer, so that they assure a better observation or the tympanic repair process.

The merit of the application of estereal derivatives of hyaluronic acid has to be attributed to the characteristic of slow release of the active principle (hyaluronic acid), in times which are directly proportional to the esterefication degree thereby assuring longer stay times of the material in the tissues.

Materials and Methods

Model description 8 mature Sprague Dawley rats, being 5 months old, having a weight ranging between 350 and 400 g, made diabetic by streptozocin (STZ) treatment 60 mg/kg .p. for 30 days, have been subjected to bilateral tympanic perforation.

Use was made of the experimental method described by Martini et al.: Experimental tympanic membrane perforation, natural history of healing process in rat; Acta otorhinol, ital.; 10,559–577,1990.

Summing up, every animal was anaesthesized by intraperitonaeal injection of sodium pentabarbital (Nembutal®), 45 mg/kg and then subjected to bilateral perforation of the hinder-upper quadrant of the pars tensa of the tympanic membrane, carried out at the operating microscopy with lanceolate bistoury.

Treatment conditions
  the tympanic membrane of the left ear was dressed with a little spongy tampon consisting of lyophilized HYAFF7, having cylindrical form and being imbued with a drop of a physiological solution. In order to assure the permanence of the little tampon, a scarification was carried out of the walls of the external auditive duct, thereby causing a bleeding sufficient for the formation of a clot;
  the tympanic membrane of the right ear was used as control. The tympanic membranes of the animals were examined at the operating microscopy on the 1st, 4th, 6th, 8th, 11th and 13th day.

Results

The results obtained by examining the tympanic membranes at an operating microscopy show that:
  1—all the tympanic membranes treated with HYAFF proved to be repaired 8 days after the treatment, whereas only 50% of the tympanic membranes, which had not been treated, showed the same results (the repair completion of the right tympanic membranes, which had not been treated, occurred after 11–13 days);
  2—the tympanic membranes treated with HYAFF proved to be (at the last otoscopic test, i.e. on the 13th day) of better quality: shining, not opaque, without chromatic variations or dimorfirms.

Concluding, from the above cited data, the application of the spongy material consisting of esters of lyophilized HA proved to be valuable, as it favours, in a diabetic rat, a tympanic repair of better quality and in shorter times, when compared with a spontaneous repair.

The above disclosed clinic and experimental results, show that both pharmaceutical preparations of spongy material consisting of lyophilized HA and lyophilized HYAFF are active and effective in tympanic perforation therapy and more generally in otologic microsurgery.

The new slow release spongy material consisting of hyaluronic acid or its derivatives is obtained by the following process, forming a further object of the present invention.

Preparation process

1. Dissolution of the active principle

In a suitable apparatus, equipped with a heating system, suitable stirring and vacuum/nitrogen pressure/sterile filtrate system, hyaluronic acid, or one of its estereal derivatives, is dissolved in water for injectable preparations, so as to reach a concentration ranging between 1 mg/ml and 40 mg/ml.

2. Solution filtration

The solution containing hyaluronic sodium salt is filtered suitably through a sterilizing membrane, having a porosity of 0.2 micrometers, afterwards it is collected in a sterile environment.

3. Solution distribution

The filtered solution is parcelled out in a sterile environment, into suitable sterile containers, such as tiny bottles, blisters and the like, by dosing the solution so as to achieve 10 mg of active principle in each container.

4. Lyophilization

The containers, after having been filled up, are put into a lyophilization apparatus and the product is frozen to a temperature ranging between 0° C. and −90° C.; the temperature decrease for achieving the freezing is captied out at rates ranging between 1° C. every 20 seconds and 1° C. every 3 hours.

Drying step by high vacuum (residual vacuum in the chamber ranging between 1000 and 1Hg mm) and heating step with plate temperature ranging between −90° C. and +60° C., follow.

Both the cooling step and the heating step are handled by means of a computer, programmed as follows:
  temperature decrease for freezing, value ranging between 1° C. every 20 seconds and 1° C. every 3 hours.
  temperature increase for sublimation, value ranging between 1° C. every 20 seconds and 1° C. every 8 hours.

At the end of the lyophilization the tiny bottles are stoppered in a sterile way.

The tiny bottles of lyophilized product are drawn out from the sterile container at the time of use.

The thus obtained spongy material consists of hyaluronic acid or its derivatives and appears from a macroscopic point of view, as a higly microporous spongy little disk, being preferably between 0.2 and 2 cm high and having a diameter ranging poreferably between 0.5 and 4 cm, having a residual humidity content ranging between 0.01% and 10%, being very hydrophilie and easily manageable, which spongy material, after having been compressed, can assume the shape of a discoid still sufficiently elastic, so that it can be applied easily and brought into contact with the lesion to be treated.

Moreover the new spongy material, according to the invention, both the one coming from HA and the one coming from an ester of it, has the following characteristics:

apparent volume: ranging between 0.04 and 27 ml;
apparent density: ranging between 0.00037 and 0.25 g/ml;
actual volume: ranging between 0.001 and 2.5 ml;
actual density: ranging between 0.004 and 10 g/ml.

In particular a "little sponge" obtained from HA or a little sponge obtained from HYAFF, according to the process as described hereinbefore, were tested at a scanning electronic microscope (SEM Philips 505). As it results from the enclosed figures, of which FIG. 1 relates to the material obtained from HA and FIG. 2 relates to the material obtained from HYAFF, in both cases the materials appear as sponges having a lamelar structure, whose porosimetry can be drawn directly from the image, since the reference at the foot of each photograph as a white bar corresponds to 1 mm in length.

Figure 2:
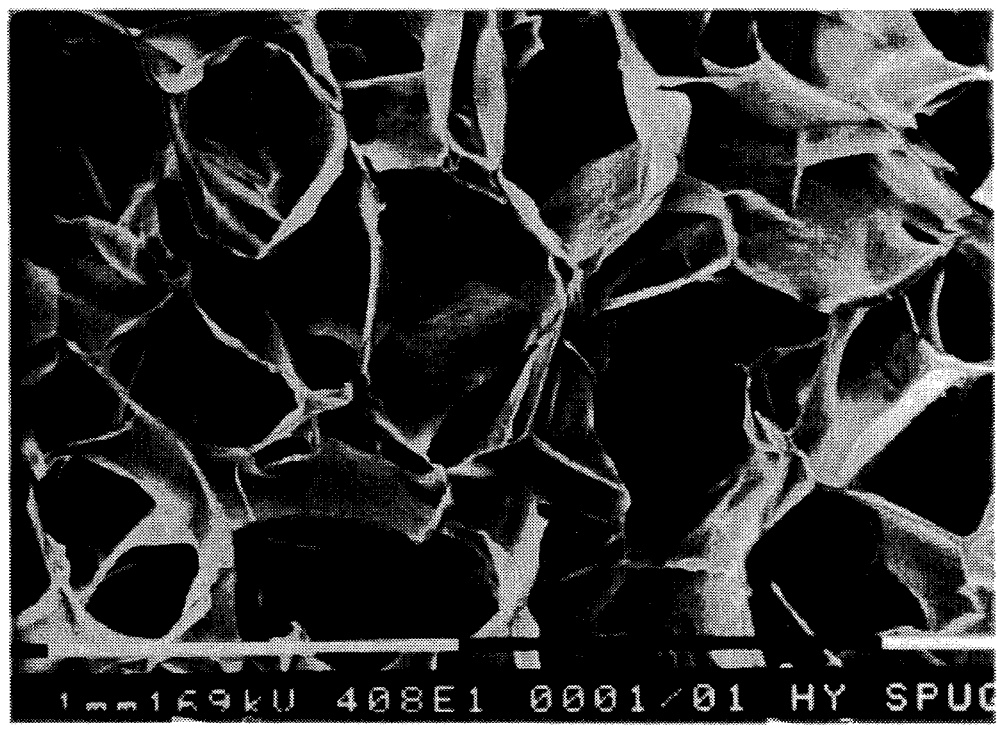
FIG. 2 is a scanning election photograph of a spongy material obtained from HYAFF, wherein the white bar represents 1 mm.

Though the two materials present a very similar structure, they differ from each other owing to the filling compactness, which is 6–10 times thicker in the sample of lyophilized HA (FIG. 1), compared with the one of HYAFF (FIG. 2). A microstructural characteristic of the lyophilized HA sample consists in the constant presence, in the lamellae forming the spongy filling, of micropores, which, on the contrary, do not appear in the HYAFF lamellae.

We can suppose that the slacker filling and the more uniform structure of the HYAFF lamellae contribute to give the improved characteristics of mechanical resistance and resilience, which can be observed on the HYAFF dry material.

We claim:

1. A sterile slow release spongy material in a dose for a single topical application consisting essentially of a lyophilized non-crosslinked hyaluronic acid ester, said spongy material having an apparent volume ranging between 0.04 and 27 ml, an apparent density ranging between 0.00037 and 0.25 g/ml, an actual volume ranging between 0.01 and 2.5 ml, and an actual density ranging between 0.004 to 10 g/ml.

2. The sterile spongy material in a dose for a single topical application, according to claim 1, wherein said ester of hyaluronic acid is hyaluronic acid ethyl ester.

3. The spongy material, according to claim 1, in the shape of a microporous disk.

4. The spongy material, according to claim 3, wherein said microporous disk has a height of between 0.2 and 2 cm and has a diameter ranging between 0.5 and 4 cm.

5. The spongy material, according to claim 1, having a residual humidity ranging between 0.01 and 10%.

6. A method for treating wounds, which comprises applying to said wounds a sterile spongy material in a dose for a single topical application consisting essentially of lyophilized non-crosslinked hyaluronic acid or a derivative thereof.

7. A method of repairing tympanic wounds, which comprises applying to said tympanic wounds a sterile spongy material in a dose for a single topical application consisting essentially of non-crosslinked hyaluronic acid or a derivative thereof.

8. The method according to claims 6 or 7, wherein said derivative of hyaluronic acid is an ester of hyaluronic acid.

9. The method according to claim 8, wherein said ester is hyaluronic acid ethyl ester.

10. The method according to claims 6 or 7, said sterile spongy material in a dose for a single topical application having an apparent volume ranging between 0.04 and 27 ml, an apparent density ranging between 0.00037 and 0.25 g/ml, an actual volume ranging between 0.01 and 2.5 ml, and an actual density ranging between 0.004 and 10 g/ml.

11. The method according to claims 6 or 7, wherein said sterile spongy material in a dose for a single topical application is in the shape of a microporous disk.

12. The method according to claim 11, wherein said microporous disk has a height of between 0.2 and 2 cm and has a diameter ranging between 0.5 and 4 cm.

13. The method according to claims 6 or 7, said sterile spongy material in a dose for a single topical application having a residual humidity ranging between 0.01 and 10%.

* * * * *